(12) United States Patent
Price

(10) Patent No.: US 6,983,184 B2
(45) Date of Patent: Jan. 3, 2006

(54) INTERACTIVE-MODIFIED INTERACTIVE EVENT RELATED POTENTIAL (IMIERP)

(75) Inventor: Gregory Walter Price, Mount Crosby (AU)

(73) Assignee: Gregory W Price, Maida Vale (AU)

( * ) Notice: Subject to any disclaimer, the term of this patent is extended or adjusted under 35 U.S.C. 154(b) by 660 days.

(21) Appl. No.: 10/142,834

(22) Filed: May 13, 2002

(65) Prior Publication Data

US 2003/0004429 A1 Jan. 2, 2003

(51) Int. Cl.
*A61B 5/0484* (2006.01)

(52) U.S. Cl. .............................. 600/544; 600/13; 607/45
(58) Field of Classification Search ................. 600/544, 600/9, 13, 14, 15; 607/45
See application file for complete search history.

(56) References Cited

U.S. PATENT DOCUMENTS

| 4,408,616 | A | * | 10/1983 | Duffy et al. ................. 600/544 |
| 4,493,327 | A | * | 1/1985 | Bergelson et al. ........... 600/544 |
| 5,116,304 | A | * | 5/1992 | Cadwell ........................ 600/13 |
| 5,707,334 | A | * | 1/1998 | Young ............................ 600/9 |
| 6,266,556 | B1 | * | 7/2001 | Ives et al. .................... 600/544 |
| 6,488,617 | B1 | * | 12/2002 | Katz ............................ 600/544 |

* cited by examiner

*Primary Examiner*—Eric F. Winakur

(57) ABSTRACT

A method modifying a particular electrophysiological feature generated in response to a stimulus is disclosed. The method involves a repeated process of: sampling the brain wave state in order to apply a modifying pulse; modifying the brain wave state to a state more conducive to a required response; sampling the brain wave state in order to apply a response stimulus; applying a stimulus only when the brain wave state substantially meets the preselected response criteria; recording the brain wave activity of the subject subsequent to the application of the stimulus.

7 Claims, 2 Drawing Sheets

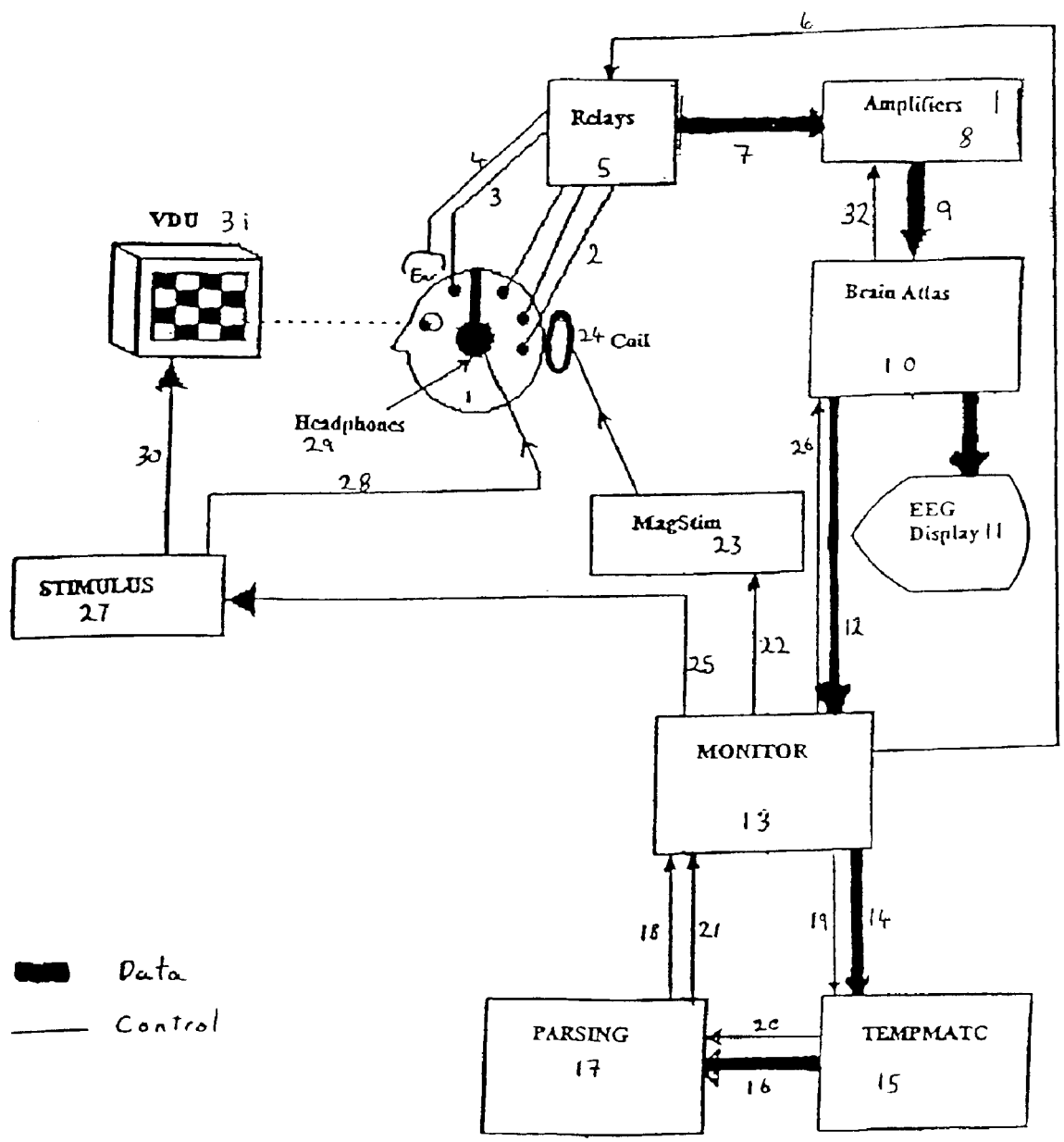
Fig : 1

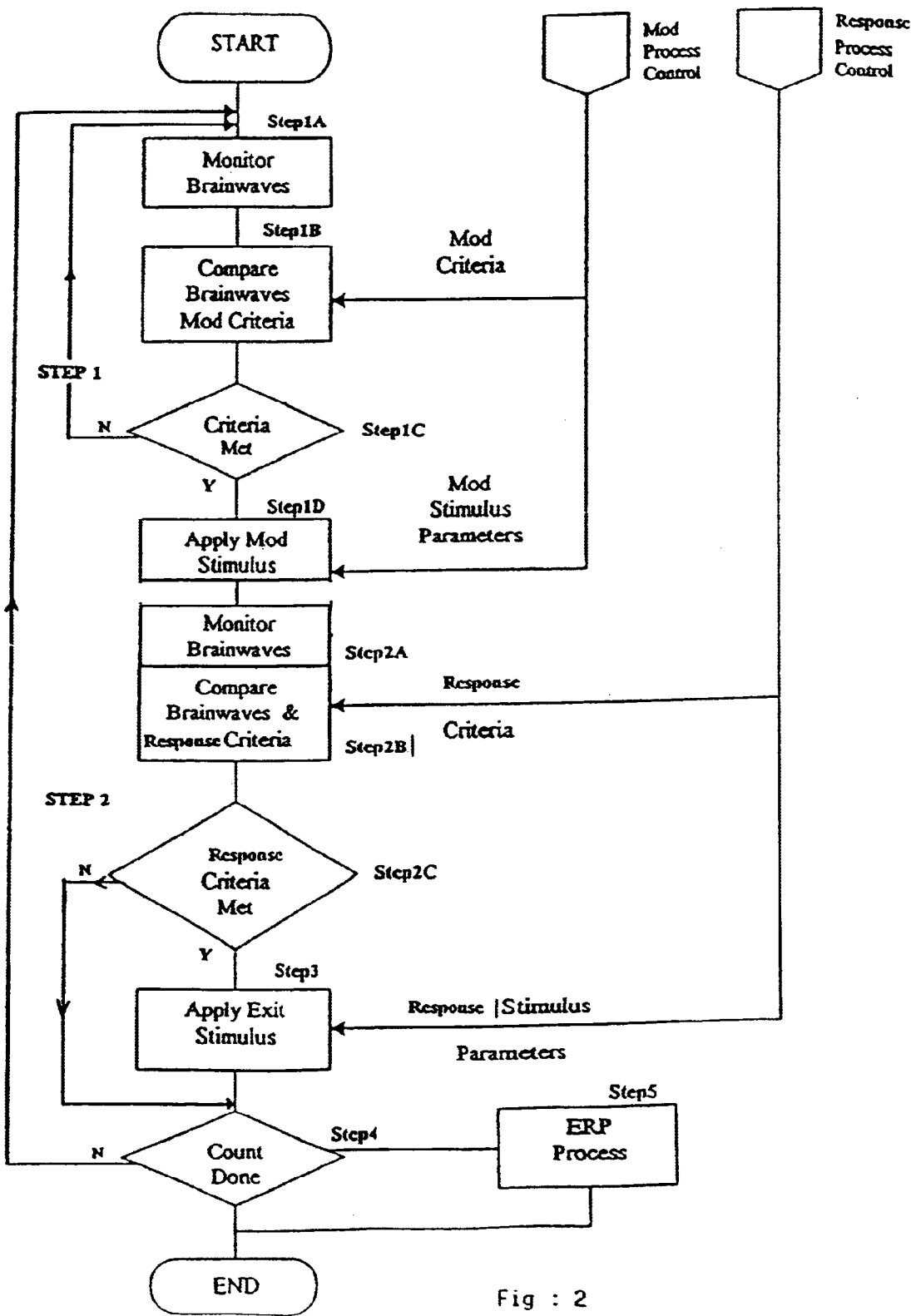
Fig : 2

INTERACTIVE-MODIFIED INTERACTIVE EVENT RELATED POTENTIAL (IMIERP)

STATEMENT REGRADING FEDERALLY SPONSORED RESEARCH OR DEVELOPMENT

None.

TECHNICAL FIELD OF THE INVENTION

This invention relates to the area of electrophysiological measurement and analysis in the field of neurosciences. More particularly it relates to a method for modifying and acquiring event-related features representative of physiological activity in the brain of a subject, for example event-related potentials (ERPS) obtained from electroencephalographic signals or event-related fields (ERFS) obtained from magnetoencephalographic signals.

The invention also relates to the field of trans- cranial stimulation of the brain.

BACKGROUND ART
Definitions

| | |
|---|---|
| EEG: | Electroencephalogram. |
| MEG: | Magnetoencephalogram. |
| ERP: | Event Related Potential. |
| IERP: | Interactive Event Related Potential. |
| IMIERP: | Interactive Modified Interactive Event Related Potential. |
| ISI: | Inter Stimulus Interval. |
| PR: | Pattern Recognition. |
| TMS: | Trans-cranial Magnetic Stimulation |
| rTMS | Repetitive Trans-cranial Magnetic Stimulation |
| TES: | Trans-cranial Electrical Stimulation |
| MAP: | Motor Action Potential. A nerve signal sent to muscles. |
| BWS: | Brain-wave-state |
| Modifying pulse: | An input intended to predictably modify the subsequent brain-wave-state. |
| TMS-Pulse: | Electromagnetic modifying pulse. |
| Modifying criteria: | PR features, which identify a brain-wave-state in which a modifying pulse is likely to modify the BWS in a predictable manner. |
| Response feature: | The electrophysiological feature, which results from the use of the disclosed process. Usually but not necessarily analogous to an ERP. |
| Response Inducing Stimulus: | An input intended to produce an electrophysiological feature for further analysis. Usually but not necessarily an external sensory input. |
| Response criteria: | PR features which identify a brain-wave-state in which a response inducing stimulus is likely to modify the BWS in a predictable manner so as to produce the desired modification of the response feature. |
| Exit criteria: | Non BWS features, which are used to manage the operation of the process. Exit features may be local to a particular step, or apply to the whole process. They are usually time or count values. |

EEG

Electroencephalography is a non-invasive investigative technique, which finds application, inter alia, in the diagnosis, prognosis and treatment of mental illness. A conventional electroencephalogram (EEG), which is a recording of a time varying potential corresponding to brain electrical activity, can be detected and recorded using electrodes placed in proximity to the scalp of a human subject. The complementary technique of magnetoencephalography (MEG) similarly measures the magnetic signals emitted by the brain

ERP

Event related potentials (ERPS) reflect the variations in brain electrical activity deriving from physiological processes, which are associated with the occurrence of some definable event, or psychological process, such as a movement or an external stimulus. Similarly event related fields (ERFS) reflect the variations in brain magnetic activity associated with such an event. ERPs are conventionally extracted from EEG data, in which they are embedded, by a procedure known as "averaging". Single sweep ERPs may also be recorded and analyzed, without using averaging. In this document, the term ERP is used for either method.

While the averaged ERP waveform is often treated as an entity in its own right, it should be noted that it is only a convenient representation of more complex entities. The averaged ERP is derived from variations in ongoing brain electrical activity. These variations in ongoing activity are in turn believed to be physiological manifestations of cognitive processes in response to a stimulus. While a method for modifying and acquiring an ERP waveform by producing a modified response is primarily described in the disclosed process, the production of modified physiological activity or modified cognitive states is equally a valid description of the result of this process.

TMS

Direct stimulation of the brain was first demonstrated with exposed portions of the cortex. Trans-cranial stimulation seeks to produce similar effects through an intact skull.

High voltage, single pulse, percutaneous electrical stimulation of the human motor cortex has been used since 1980 (Merton P. A. and Morton H. B. (1980), "Stimulation of the cerebral cortex in he intact human subject", Nature 285, pp227). Anodal voltages of about 150 V are applied at the vertex with a cathode to one side. Evidence of effect includes MAPs and phosphenes.

Trans-cranial stimulation of the cortex seeks to produce electrical currents in the cortex, sufficient to alter the operation of localized neurons. Trans-cranial Magnetic Stimulation (TMS) is implemented by passing a time varying electric current through a coil held close to the head. The resultant magnetic field passes through the skull, and induces a small secondary current in the cortex, which probably leads to depolarisation of cortical neurons.

The progress from single magnetic pulses to rapid repetitive Trans-cranial Magnetic Stimulation (rTMS) was a logical development. Behavioral effects have been demonstrated with depression (Pascual—Leone et al, 1994b; Hoflich et al., 1993; George et al., 1995), and schizophrenia (Grisaru et al., 1994) None of these processes is dependent upon the current electrophysiological activity, nor utilises the immediate effects of stimulation on the electrophysiological activity.

Terminology

The term "brain wave state" as used in this document refers to spatio-temporal patterns of brain physiological activity, such as the patterns of brain electrical activity revealed by an EEG recording, and/or patterns of brain magnetic activity as revealed by an MEG recording. These patterns are similar in concept to the microstates as described by Lehman et al. 1987 ("EEG alpha map series: brain micro-states by space orientated adaptive segmentation", Electroenceph Clin. Neurophysiol., 67 271–288), although the specific implementation may vary. The microstate description is simply the closest current electrophysiological concept to the BWS. In concept, the BWS is assumed to represent a distinct brain state, as vaguely used in cognitive psychology, although the process does not rely on this feature. The brain wave states as used herein are preferably less then one second in is duration although longer states may be useful for particular applications, for example in detecting drowsiness. In practice, the BWS is simply a short-term pattern of brain waves (EEG/MEG) identified by PR techniques.

The terms "pulse" and "stimulus" are, for clarity of presentation used for inputs at different stages of the process. The differences in physical parameters of each input, however, are not critical. The purpose of the stimulus within the process is however critical. A modifying pulse is intended to predictably modify the subsequent brain-wave-state. A response-inducing stimulus is intended to produce a modified electrophysiological feature for further analysis. While the preferred implementation uses TMS as a modifying pulse, and auditory tones as a response-inducing stimulus, alternative implementations are also detailed. While in this embodiment all pulses and stimuli are externally generated, that is not a requirement of the process. The process could use endogenous inputs as either a modifying pulse or a response-inducing stimulus, provided such an input was reliably identified and precisely measured in time. Similarly the brain wave state pattern recognition criteria are of two types. Modification criteria, and response criteria.

The terms brain wave state, and ERP as used in this document require special clarification. They each arose from different fields of research as discussed earlier. They are used, for convenience of presentation, in different ways and at different stages of the process. They are likely to have slightly different parameters (e.g. 300 milliseconds for ERP and 1000 millisecond for brain-state), and to have different connotations (e.g. ERP usually averaged, brain-state is usually not in response to stimulus). However, it should be clearly noted that electrophysiologically they are the same. Both represent a brief pattern of electromagnetic radiation from the brain as a result of various physiological processes.

Prior Art ERP

The article entitled "P300 clinical utility and control of variability" (Polich, 1998.*J. Clin. Neurophysiol*) is an example of the use of the standard ERP process. No modifying pulse is applied, and the response-inducing stimulus is applied at random within set ISI limits. The response-inducing stimulus is again an auditory target (2000 Hz) or non-target (1000 Hz). Although the response inducing stimulus is similar, and inter stimulus intervals may be similar, the standard process makes no attempts to modify the brain wave state and applies response inducing stimuli without regard to the current brain wave state.

Goodin 1990 ("Clinical utility of long latency 'cognitive' event related potentials (P3): the pros", *Electroenceph Clin. Neurophysiol.*) analyzed certain patient studies conducted during the 1980s, and found that there were discrepancies amongst the studies regarding the sensitivity of the P3 (or P300). This author observed that this may relate to differences in the method of eliciting the P3 response, variability in the severity of dementia among the patients studied and the fact that some patients do not generate a recognizable or reproducible response. Furthermore inattention can, even in normal subjects, result in either a small or absent P3 response. Goodin concludes that a high rate of absent or non-reproducible P3 responses will detract from its clinical utility and that this rate differs widely between investigators. This work thus identifies several consequences of ERP studies that are based on stimuli that are applied in non-optimal brain wave states. These include lower amplitude, longer latency, and greater variability of single sweep responses. The report makes no suggestions, however, as to how these shortcomings may be overcome. The interactive ERP detailed next was a development that addressed several of the reported problems.

EEG/ERP correlates of cognitive function have been studied in neuropsychology (Pritchard, W. S. (1981) Psychophysiology of P300. *Psychological Bulletin*, 89(3), 506–540. The current state of this art is best shown by Gevins et al. 1998 ("Mapping cognitive brain function with modern high resolution electroencephalography," TINS 18(10) pp429–436.

Prior Art Interactive ERP (IERP)

In ERP studies, the important assumptions are identical stimuli, reproducible responses to a particular randomly applied stimulus and random stationary background EEG activity that is not correlated with the ERP. Several authors have questioned the assumption of independence of the ERP and background EEG, including Basar et al. 1984 ("A new approach to endogenous Event Related Potentials in man: Relation between EEG and P300 wave", *Interm. J. Neuroscience*, 24 (Suppl.1) 1–21) and Squires & Donchin 1976 ("Beyond averaging: The use of discriminant functions to recognize event related potentials elicited by auditory stimuli", *Electroenceph Clin. Neurophysiol.* 41 449–459).

Various models have described the endogenous potentials, for example the P300 wave, as a dynamic change in the EEG activity already present (Stampfer 1988, "An analysis of preparation and response activity in P300 experiments in humans", in Basar and Melnechuk (Eds.), *Dynamics of sensory and cognitive processing by the brain* (1st Edition), Springer-Vertag, Berlin, 275–286, and Wright et al. 1990 "Inverse filter computation of the neural impulse giving rise to the auditory evoked potential", *Brain Topography*, 2 293–302). A number of authors have previously described effects of pre-stimulus brain wave state, specifically alpha waves, on the ERP, Jasiukaitis & Hakerem 1988 ("The effect of pre-stimulus alpha activity on the P300", Electroenceph Clin. Neurophysiol, 25 (Suppl. 2) 157–65) found that larger amplitude P300s were obtained in the high alpha ERP. Stampfer 1988 (supra) reports on an increase in alpha phase alignment with the onset of stimulus, but does not correlate this increase with resulting averaged amplitude. Jansen & Brandt, 1991 ("The effect of the phase of pre-stimulus alpha activity on the averaged visual evoked potential", *Electroenceph Clin. Neurophysiol.*, 80 241–250) carry out this correlation of alpha phase with amplitude for a visual evoked response.

These previous studies selected EEG data retrospectively for further analysis. However, the P300 and long latency potentials in general can be affected by a large number of factors other than background EEG, such as the ordering of preceding stimuli, the inter stimulus interval (ISI), refractory periods and habituation effects. Accordingly, such retrospective selection leads to difficulties in obtaining a data set balanced for all factors other than the variable under test. The interactive ERP ("The effect of pre-Stimulus alpha activity on the auditory P300 paradigm: a prospective study", *Brain Topography*, 9(3) 169–176) detailed a way of addressing this problem.

Australian Patent Application No. 39994797 in the name of Price discloses the "interactive ERP" (IERP) system for acquiring event related potentials (ERPs) based on the background EEG. This interactive measurement system is essentially a passive probe, with information being derived from the analysis of naturally occurring bran wave patterns.

Conceptually the IERP process is a methodology from both EEGs and ERPS. The process provides new information that is simply not obtainable by the EEG or standard ERP processes. This information, how the ERP interacts with the brain wave state of the EEG, has the potential utility of any new measure in research and clinical practice.

In practice, however, it may at present be considered as an adaptation of the standard ERP technique. The major advantage of the IERP process (and hence of the disclosed process) over the standard ERP process is that it provides a means of modifying the feature of interest, through superior theoretical support. The process has been shown to produce an IERP which is significantly different to the standard ERP for a particular brain wave state ("The effect of Pre-stimulus alpha activity on the auditory P300 paradigm." Price G. W., 1997, Brain Topography). In addition, the IERP has increased scientific validity as the background EEG in the typical standard ERP consists of varying length periods of several brain wave states, the resulting standard ERP is the result of an uncontrolled mixture of ERPs to each brain wave state. The IERP process allows the investigation of a pure (based on a single brain wave state) ERP, instead of a mixture. The advantage is obtained by the process allowing the control of a variable (brain wave state) which has been shown to have an effect on the ERP.

The article entitled "Enhancement of visual evoked potentials by stimulation during low Pre-stimulus EEG stages,", Rehn and Basar, 1996) makes an attempt to apply response inducing stimuli based on background EEG characteristics such as spectral content. These general characteristics are not, I believe, the same as the brain wave states used in the disclosed process. The Rehn and Basar process, in any case, makes no attempt to modify the background EEG characteristics.

The interactive ERP process has the difficulty of having to wait for a requisite brain wave state to occur by chance. If a brain wave state being investigated has a particularly low incidence by chance, then the interactive ERP process may not be able to operate effectively. Either a large inter stimulus interval, or a low number of stimuli will prevent a representative ERP from being generated. The present invention, overcomes that problem by artificially modifying the brain wave state, to increase the incidence of the requisite state, either as an end in itself, or prior to interactive ERP recording.

Prior Art TMS

U.S. Pat. No. 4,940,453 in the name of Cadwell discloses a method for magnetically stimulating neural pathways of a human, and also a method of generating ERPs based on these stimuli. The method disclosed however, delivers stimuli at random, or at a predetermined stimulus rate, and takes no account of the background brain wave state. The present invention takes account of the background EEG state before initiating stimuli.

Prior Art Various

Other relevant prior art known to use techniques similar to ERP exists in the fields of biofeedbacks, photic driving, "conditioning stimuli" and "self-generated ERPS".

Biofeedback in the ERP context is a field in which a feedback stimulus is applied after a standard ERP has been generated and analyzed. The process differs from the current process in three ways. The modification is very indirect, being via some form of cognitive involvement. The modification is directed at the response, rather than the pre-stimulus brain wave state. The modification is applied, and evaluated, over large time frame.

Photic driving "entrainment" is an EEG related field in which a regular repetitive stimulus is applied to produce a desired periodic brain wave state, irrespective of the pre-existing brain wave state. This entrained (usually alpha frequency) signal provides general information about the response of a periodic brain waveform to a regular periodic stimulus. The information provided during entrainment is conceptually different to the single brain wave response to a single stimulus form of information provided by an ERP.

The information is distributed over many cycles of the response, is limited to characteristics of a given periodic signal, and most importantly the information is limited to brain wave states which have been shown to respond to photic driving, such as alpha waves. A refinement to this method is to use information from an existing periodic waveform to synchronize the stimulating waveform with the brain waves of the subject such as described in U.S. Pat. No. 5,241,967 in the names of Yasushi and Saito.

Self-generated ERPs are event-related potentials in response to the subjects own stimulus marker, typically a button press. No external stimulus is provided, and the subject is required to initiate the stimulus when in a selected mental state. Mental state, however, is not necessarily the same as brain wave state and is dependent on a subjective judgement by the patient. In addition, there is no modification.

In conditioning stimulus paradigms, a conditioning stimulus (CS) is applied in order to force the subject into a required mental state before the application of the operative imperative stimulus (IT). It differs from th current process in that both stimuli are applied at random. Neither CS nor IS are based on the actual brain wave state.

OBJECT OF THE INVENTION

It is an object of the present invention to provide a novel method for modifying electrophysiological features of the brain, to produce a requisite brain-wave-state.

It is another object of the present invention to provide a method for acquiring event-related data, representative of physiological activity in the brain, which overcomes or at least ameliorates some of the problems associated with the prior art for acquiring ERP data.

It is another object of the present invention to provide a method for modifying cognitive, physiological, or behavioural features, which are putatively associated with the electrophysiological features.

Further objects will be evident from the following description.

DISCLOSURE OF THE INVENTION

In one form, although it need not be the only or indeed the broadest form, the invention resides in a process for modifying a particular electrophysiological feature generated in response to a stimulus. While this feature is naturally modified by quasi-random variations in the pre-stimulus brain wave state, the disclosed process artificially induces an identified pre-stimulus brain wave so as to predictably modify the response feature. Artificial modification of the pre-stimulus brain wave state is carried out by application of a modifying pulse, in this instance a Trans-cranial Magnetic Stimulus (TMS) pulse.

The essential feature of the process is the artificial production of an identified brain wave state prior to the application of a response-inducing stimulus.

Said method including the steps of:

Step1

Step1A Continuously monitoring the subject's brain wave state;

Step1B Comparing the monitored brain wave state with pre-selected criteria;

Step1C If the brain wave state substantially meets the pre-selected modification criteria go to Step1D, else go to Step 1A.

Step1D Apply modifying pulse and go to Step2.

Step2

Step2A Continuously monitoring the subject's brain wave state;

Step2B Comparing the modified brain wave state with pre-selected response criteria;

Step2C If the brain wave state substantially meets the pre-selected response criteria go to Step3, else go to Step4;

Step3

Apply a response-inducing stimulus, and record the brain wave activity of the subject subsequent to the application of the response-inducing stimulus;

Step4

Optionally adjusting modification criteria and response criteria. If all stimuli are delivered go to Step5, else return to Step1.

Step5

Processing the recording of brain wave activity to extract the electrophysiological response for further analysis.

A detailed flow chart of the process is given in FIG. 2.

Step1A and Step2A:

Preferably the step of monitoring the subject's brain wave state includes the step of periodically sampling spontaneous potential(s) sensed at one or more scalp locations of the subject.

Alternatively, the step of monitoring the subject's brain wave state includes the step of periodically sampling spontaneous magnetic field(s) sensed proximate one or more scalp locations of the subject.

In preference, the step of monitoring brain wave state of the subject the step of determining the nature of background brain wave activity, from the sense spontaneous potentials or fields, in real time.

Step1B and Step2B:

Preferably the pre-selected criteria in the comparing step are representative of a desired brain wave state.

Preferably, the pre-selected criteria are representative of a brain wave state which is known to be modified in a predictable manner.

Alternatively, the pre-selected criteria are representative of a brain wave state associated with a particular illness or disability. The process is then used to analyze how such a BWS modifies the resulting response feature. The pre-selected criteria may also include a pattern of brain wave activity selected in order to investigate a mental dysfunction.

Suitably the pre-selected criteria include a selected threshold amplitude, frequency distribution and/or wave shape of background brain wave activity.

Preferably, the comparing step employs syntactic analysis techniques in order to compare the monitored brain wave state to the representative criteria.

Alternatively, the step of monitoring brain wave activity may involve fast Fourier transform, auto correlation or template matching techniques.

Step1C:

Preferably, the modifying pulse would be a trans-cranial magnetic stimulation pulse.

Alternatively, the modifying pulse would be a trans-cranial electrical stimulation pulse.

Alternatively, the modifying pulse would be a sensory stimulus. Sensory stimuli may be selected from applying one or more of an auditory, visual, olfactory, gustatory, tactual, or somatosensory stimulus.

Step2C:

Preferably the response criteria in this step are different to the modifying criteria in Step 1C.

Preferably the criteria in this step are representative of a different brain wave state.

Preferably, the step of applying the response-inducing stimulus may be selected from applying one or more of an auditory, visual, olfactory, gustatory, tactual, or somatosensory stimuli analogous to those currently used in ERP studies.

Alternatively, the response-inducing stimulus may be a final TMS/TES pulse, intended to evoke a single response.

Alternatively, the step of applying a pre-selected stimulus may include the step of selecting the stimulus, from a range of available stimuli, in accordance with the brain wave activity of the subject recorded in a previous cycle or step.

Alternatively, the step of applying a response stimulus may be carried out after a predetermined time delay.

Alternatively, the final modifying pulse (Step 1C) can be considered as the response-inducing stimulus. In this alternative, the final modified brain wave state is considered as the response feature.

Step3:

Preferably the step of recording the brain wave activity of the subject includes the step of recording one or more brain wave states of the subject.

Suitably, the step of recording the brain wave activity of the subject includes the step of recording the occurrence of the stimulus applied to the subject.

The step of recording the occurrence of the stimulus may include the steps of recording the time, duration and/or type of stimulus applied to the subject.

Preferably the step of recording said one or more brain wave states of the subject includes the step of periodically sampling and is recording potential(s) sensed at said scalp locations of the subject.

Alternatively, the step of recording said one or more brain wave states of the subject includes the step of periodically sampling and recording field(s) sensed proximate said scalp locations of the subject.

Step4:

Preferably, each cycle of the process involves a single modifying pulse (Step1) for each response-inducing stimulus (Step2).

Alternatively, several modifying pulses (Step1) may be needed before the predicted brain wave state modification is achieved, and a response-inducing stimulus can be applied. In this alternative, modifying pulses that do not lead to a BWS matching the response criteria are considered as ineffective.

Alternatively, a series of modifying pulses may be needed to modify the brain wave state via a predictable sequence of intermediate brain wave states. In this alternative, a modifying pulse that does not lead directly to a response stimulus is still considered effective if a predicted modification of the BWS is achieved.

Preferably, the modifying pulse has the same characteristics for each process cycle, and for each cycle of Step1.

Alternatively, the modifying pulse may varied for each pulse application. Variation may involve TMS voltage, period, polarity, or location. The pulse modality may also be varied (e.g. electrical or sensory pulses).

Preferably, the response-inducing stimulus has the same characteristics for each process cycle, and for ech cycle of Step2.

Alternatively, the response-inducing stimulus may varied for each stimulus application. Variation may involve sensory parameters such as amplitude, period, frequency, or location. The stimulus modality may also be varied (e.g. visual, electrical or TMS stimuli).

Preferably, the modifying criteria remain the same for each cycle of the process. Alternatively, the modifying criteria may be varied for each cycle of the process, or for each pass of Step1.

Preferably, the response criteria remain the same for each cycle of the process. Alternatively, the response criteria may be varied for each cycle of the process, or for each pass of Step2.

Preferably, each cycle of the process begins with the same initial values for modifying pulse, modifying criteria, response inducing stimulus, and response criteria.

Alternatively, initial values may be varied for each cycle, based on either wave state information (learning), or on independent parameters such as recording time or stimulus count.

Step5:

Preferably steps 1 to 4 of the method are repeated for a predetermined number of cycles in order to assemble a plurality of brain wave activity recordings in response to said stimulus.

Preferably Step 5 employs signal averaging processing techniques. Alternatively, any one of several single sweep analysis techniques could be employed.

Preferably, the response feature is based on the recorded brain wave state. Alternatively, where the putative brain wave state is undetectable, or unidentified, or unidentifiable, the response feature may be characterized by the processing of non-electrophysiological data. Such data may be behavioural (e.g. reaction time), clinical (e.g. rating scales) or subjective (e.g. self-report scales).

BEST MODE FOR CARRYING OUT THE INVENTION

To assist in understanding the invention, preferred embodiments will now be described with reference to the following figures in which:

FIG. 1 is a schematic diagram of a system operating in accordance with an embodiment of the invention;

FIG. 2 is a flow chart illustrating key steps in the method of a first embodiment;

The embodiment described is that initially used, and is largely determined by available equipment. While several different computers are used to carry out the process, it would be obvious to anyone with skill in the art, that the process could be implemented with fewer computers, and even on a single combined unit. A representative application of the process (P300 paradigm) is also detailed.

BRIEF DESCRIPTION OF DRAWINGS

Whilst the "interactive-modified interactive" ERP (IMIERP) method of the invention can be readily applied to many types of electrophysiological investigation of the brain, the particular system illustrated in FIG. 1 is arranged for the conduct of an investigation into the P300 peak generated in an auditory oddball paradigm (supra). Thick lines in FIG. 1 are intended to indicate data flow (usually multi channel), while thin lines represent control information.

The system includes an array of fourteen electrodes (2) disposed in substantially the standard 10–20 (minus F7, F8, T5, T6, FP1 and O1) arrangement at respective sites on the scalp of a subject (1): All electrode sites are referenced to earlobes (4) of the subject 11, and a ground lead (3) is used. Thus sixteen analogue signal lines feed into the normally closed relays (5).

The signals from the electrodes feed from the relay unit (5), to the amplification and filtering state (8) before being passed (9) to the Brain Atlas (BA) (10) where they are sampled and digitized. All signal channels have a nominal gain of 30,000, a lower band pass (−3 dB attenuation) of 1 Hertz (Hz) and an upper band pass (−3 dB attenuation) of 30 Hz the values set by the BA control lines (32). The digitized EEG data is then displayed as a continuous amplitude-time graph (11) and stored.

The amplified and filtered signals are also passed (12), undigitized, by the BA to the MONITOR computer (13). The MONITOR (13) controls the process by repeatedly executing two loops, the modifying loop, and the response loop. In both loops, DATA is generated and sent (14) to the TEMPMATIC computer (15). TEMPMATIC converts the EEG data into a string of primitives based on given criteria. These are passed (16) to the PARSING computer (17) to see if syntactic analysis criteria are met. The result (STIM) of the combined pattern recognition stage is passed (18) back to MONITOR (13). If STIM is False, the pattern recognition stage of the loop is repeated.

If Stim is true, and MONITOR is in the modifying loop, a signal is sent (6) to disconnect the relay unit (5) so that the amplifiers (8) are not saturated by a TMS pulse. A signal is also sent (22) to the Magstim unit (23). This unit delivers a TMS pulse through the coil (24). Relays are reconnected. The process then begins the response loop.

If Stim is true, and MONITOR is in the response loop. A signal, plus information on the type of stimulus, is then sent (25) to the STIMULUS computer (27). STIMULUS then delivers a Target or Non-target auditory (28) or visual (30) stimulus to the headphones (29) or VDU (31). In the embodiment the selected stimulus comprises an auditory stimulus, although it will be apparent to those with skill in the art that one or more of a visual, olfactory, gustatory, tactual, somatosensory or electromagnetic stimuli may be employed. The stimulus computer may also log responses, such as reaction time (as reflected in an optional button-press provided for the subject). MONITOR also sends a signal (26) to Brain Atlas (10) so that a stimulus marker is added to the recorded EEG. The process then begins the modifying loop.

MONITOR also does various ancillary tasks. Selection between modification or responses processes, and associated TEMPMATIC or PARSING criteria is controlled via process control lines (19,20,21). MONITOR first selects the type of stimulus. MONITOR controls the number of stimuli delivered.

Details of Flow Chart

The Flow chart FIG. 2 represents the steps outlined in the invention disclosure. The modifying and Response process inputs are separated for conceptual clarity, although technically they are carried out in the same way.

The final decision point is used to control the length of a recording session or block, which in the embodiment is determined in terms of a desired number of ERP sweeps. Step5, following the desired ERP sweeps, represents the averaging of the EEG data to produce the resultant ERP value.

REPRESENTATIVE APPLICATION OF THE PROCESS

This investigation, which is an exemplary application for the method of the embodiment of the IMIERP process, compares the amplitude of the P300 peak of the standard ERP method (which does not take account of pre-stimulus brain electrical activity), with that of the IMIERP method of the embodiment (which initiates the stimulus when brain electrical activity meets pre-selected criteria).

The P300 peak is defined as the largest positive peak occurring at the Pz scalp location in the period from 280 to 500 milliseconds (ms) from the application of the stimulus. See Polich et al. 1985 ("Effects of age on the P300 component of the event related potential from auditory stimuli: Peak definition, variation and measurement", *Journal of Gerntology*: 40(6) 721–726) and see also Polich 1991 ("P300 in clinical applications". *Am. J. EEG Technol*, 31 201–231) in relation to the standard auditory oddball paradigm.

A simple auditory oddball paradigm is utilized in the investigation, with frequent stimuli which the subject is asked to ignore and infrequently occurring "oddball" stimuli for which the subject is asked to keep a mental count. The frequent tone was of 500 Hz frequency at 60 dB nHL. The infrequent stimuli was a tone of 2000 Hz at 60 dB nHL. The stimuli were step function tones with 5 milliseconds rise time and 40-millisecond duration. The infrequent tone comprised 25% of the stimuli presented in a pseudo random fashion. The random sequence was adjusted to ensure no more than the consecutive target "oddball" tones would be generated. Both Target and Non-target tones were applied using the IMIERP process.

A series of event-related response recordings were obtained using the IMIERP process. At the same session, subsequent to each of these recordings, a series of "placebo" responses were also obtained using the standard ERP methodology. The stimulus sequence and inter stimulus interval sequence of these placebo recordings was however, identical to the preceding IMIERP recording. This allowed a direct comparison of the IMIERP process with the standard process.

The modifying pulse was applied when the brain wave state met modification criteria embodied in syntactic analysis grammar named AKTMSO3.

The response-inducing stimulus was applied when the brain wave state met response criteria embodied in a syntactic analysis grammar named AKTERPO3.

The target and non-target responses were averaged separately to extract the eletrophysiological response. In addition, the non-averaged single sweep responses were identified manually. The sets of responses obtained using the IMIERP process were compared with those using the standard process.

The IMERP and Standard responses were compared as groups using a t-Test. The data showed the IMIERP amplitude values were significantly higher than those of the Standard recording (t=2.04, df=1, p=0.046).

For a non-parametric Sign Test comparison, the responses to Targets from the IMIERP and Mapped recordings were linked. Wherever possible, equivalent stimuli were matched as per the experimental design. In some cases an equivalent stimulus was not available due to artifact elimination in either recording, and a proximal stimulus (within 15 seconds ISI) was used. In some cases where no equivalent or proximal stimulus was available, the stimulus was not matched, and was not used in these tests. The Sign test also showed that the amplitudes of the IMIERP recordings were significantly higher than those of the standard recordings (p=0.109).

Since the P300 has use as a diagnostic tool, the modification of this feature is seen as improving the diagnostic method. Similarly, as the P300 is linked by a large body of literature to cognitive processing, the modification of this feature is considered to be a modification of cognitive processing. The modification of this cognitive processing is therefore a means of treating or modifying undersired cognitive features.

The claims defining the invention are as follows:

1. A process (IMIERP process) for modifying the features of electrophysiological activity in response to a stimulus, in the brain of a subject, by interactively applying a brain-wave-state modifying stimulus, said process including the steps of:

(a) initially monitoring the subject's brain-wave-state;

(b) comparing the monitored brain-wave-state with pre-selected modifying criteria, associated with a requisite (post-modification) brain-wave-state;

(c) applying a brain-wave-state modifying pulse to the subject when the brain wave state substantially meets the pre-selected criteria, otherwise returning to step (a);

(d) monitoring the subjects modified brain-wave-state;

(e) comparing the monitored brain wave state with pre-selected stimulus-response criteria, associated with a requisite (post-stimulus) response; and (f) applying a selected response-inducing stimulus to the subject when the brain wave state substantially meets the pre-selected response criteria.

2. The process of claim 1, wherein the steps (a) to (e) are carried out repetitively before step (f).

3. A method for acquiring event related data, representative of physiological activity in the brain of a subject, sad method including the steps of:

(a) applying the process of claim 1;

(b) recording the brain wave activity of the subject subsequent to the application of the stimulus;

(c) processing the recording of brain wave activity to extract the event related data for further analysis.

4. The method for acquiring data of claim 3 wherein the steps (a) and (b) are carried out repetitively before step (c).

5. The method for acquiring data of claim 3 wherein the event related data representative of physiological activity is detected by means other than event related potentials (ERP or ERF) selected from the group consisting of:

(a) reaction time data;

(b) questionaire data;

(c) other physiological parameters.

6. A method for diagnosis of an illness (said illness being based on current diagnostic features), said illness being associated with particular electrophysiological activity in response to a stimulus, by comparing the electrophysiological activity in response to a stimulus obtained using the process of claim 1, with electrophysiological activity in response to a stimulus obtained using other stimulation processes.

7. The process of claim 1, wherein the brain-wave-state modifying pulse is one of Transcranial Magnetic Stimulation, Transcranial Electrical Stimulation, or sensory stimulus.

* * * * *